(12) United States Patent
Lai et al.

(10) Patent No.: US 11,809,080 B2
(45) Date of Patent: *Nov. 7, 2023

(54) EXTREME ULTRAVIOLET PHOTORESIST WITH HIGH-EFFICIENCY ELECTRON TRANSFER

(71) Applicant: Taiwan Semiconductor Manufacturing Co., Ltd., Hsin-Chu (TW)

(72) Inventors: Wei-Han Lai, New Taipei (TW); Chin-Hsiang Lin, Hsin-chu (TW); Chien-Wei Wang, Zhubei (TW)

(73) Assignee: TAIWAN SEMICONDUCTOR MANUFACTURING CO., LTD., Hsin-Chu (TW)

( * ) Notice: Subject to any disclaimer, the term of this patent is extended or adjusted under 35 U.S.C. 154(b) by 0 days.

This patent is subject to a terminal disclaimer.

(21) Appl. No.: 17/816,004

(22) Filed: Jul. 29, 2022

(65) Prior Publication Data

US 2022/0382156 A1    Dec. 1, 2022

Related U.S. Application Data

(63) Continuation of application No. 16/719,757, filed on Dec. 18, 2019, now Pat. No. 11,422,465, which is a continuation of application No. 15/614,032, filed on Jun. 5, 2017, now Pat. No. 10,520,813.

(60) Provisional application No. 62/434,961, filed on Dec. 15, 2016.

(51) Int. Cl.
*G03F 7/004* (2006.01)
*G03F 7/039* (2006.01)
*C07D 247/02* (2006.01)
*C07D 273/00* (2006.01)

(52) U.S. Cl.
CPC ......... *G03F 7/0397* (2013.01); *C07D 247/02* (2013.01); *G03F 7/0045* (2013.01); *G03F 7/0046* (2013.01); *G03F 7/0392* (2013.01); *C07D 273/00* (2013.01); *G03F 7/0042* (2013.01)

(58) Field of Classification Search
None
See application file for complete search history.

(56) References Cited

U.S. PATENT DOCUMENTS 10,520,813 B2 * 12/2019 Lai ............... G03F 7/0045
11,422,465 B2 *  8/2022 Lai ............... G03F 7/0392
(Continued)

FOREIGN PATENT DOCUMENTS

| JP | 2004233450 A | * | 8/2004 | |
| JP | 2010222586 A | * | 10/2010 | |
| JP | 5733167 B2 | * | 6/2015 | ............. G03F 7/004 |

*Primary Examiner* — Martin J Angebranndt
(74) *Attorney, Agent, or Firm* — HAYNES AND BOONE, LLP

(57) ABSTRACT

A method includes forming a photoresist layer over a substrate, wherein the photoresist layer includes a polymer, a sensitizer, and a photo-acid generator (PAG), wherein the sensitizer includes a resonance ring that includes nitrogen and at least one double bond. The method further includes performing an exposing process to the photoresist layer. The method further includes developing the photoresist layer, thereby forming a patterned photoresist layer.

20 Claims, 7 Drawing Sheets

(56) References Cited

U.S. PATENT DOCUMENTS

2016/0161851 A1* 6/2016 Kumaki ................ G03F 7/0397
430/296
2017/0038684 A1* 2/2017 Hirano ................ C23C 18/1605
2017/0242339 A1* 8/2017 Hatakeyama ............. G03F 7/32

* cited by examiner

EXTREME ULTRAVIOLET PHOTORESIST WITH HIGH-EFFICIENCY ELECTRON TRANSFER

PRIORITY INFORMATION

This application is a continuation of U.S. patent application Ser. No. 16/719,757 filed Dec. 18, 2019 (now issued as U.S. Pat. No. 11,422,465 B2), which is a continuation of U.S. patent application Ser. No. 15/614,032 filed Jun. 5, 2017 (now issued as U.S. Pat. No. 10,520,813 B2), which further claims the benefit of U.S. Provisional Patent Application No. 62/434,961 filed Dec. 15, 2016. The disclosures of which are hereby incorporated by reference in its entirety.

BACKGROUND

The semiconductor integrated circuit (IC) industry has experienced exponential growth. Technological advances in IC materials and design have produced generations of ICs where each generation has smaller and more complex circuits than the previous generation. In the course of IC evolution, functional density (i.e., the number of interconnected devices per chip area) has generally increased while geometry size (i.e., the smallest component (or line) that can be created using a fabrication process) has decreased. This scaling down process generally provides benefits by increasing production efficiency and lowering associated costs. Such scaling down has also increased the complexity of processing and manufacturing ICs.

For example, as the semiconductor fabrication continues to shrink pitches below 20 nm nodes, traditional i-ArF photoresists confronted a huge challenge. The optical restriction leads to resolution and lithography performance that cannot meet targets. Extreme ultraviolet (EUV) lithography has been utilized to support critical dimension (CD) requirements of smaller devices. EUV lithography employs scanners using radiation in the EUV region, having a wavelength of about 1 nm to about 100 nm. Some EUV scanners provide 4× reduction projection printing onto a resist film coated on a substrate, similar to some optical scanners, except that the EUV scanners use reflective rather than refractive optics. EUV lithography has imposed a complex set of requirements upon the resist film.

The photo acid generator (PAG) in ArF resist absorbs 193 nm wave and generates photoacid, and the acid will proceed 1000 times chemical amplifier reaction (CAR) and deprotect acid labile group (ALG). Different with 193 nm ArF resist, EUV will let sensitizer generate secondary electron. The secondary electron's energy is similar with 193 nm energy and is absorbed by PAG, which further generates photoacid and proceeds to CAR reaction after absorbing secondary electron, like 193 nm ArF resist. However, the EUV resist still suffers energy efficiency and other related issues due to chemical structure of known sensitizers, low source power for EUV tool, and factors. What are needed are a photoresist and a method using the photoresist to have improvements in this area.

BRIEF DESCRIPTION OF THE DRAWINGS

The present disclosure is best understood from the following detailed description when read with the accompanying figures. It is emphasized that, in accordance with the standard practice in the industry, various features are not drawn to scale and are used for illustration purposes only. In fact, the dimensions of the various features may be arbitrarily increased or reduced for clarity of discussion.

DETAILED DESCRIPTION

Figure 1A:
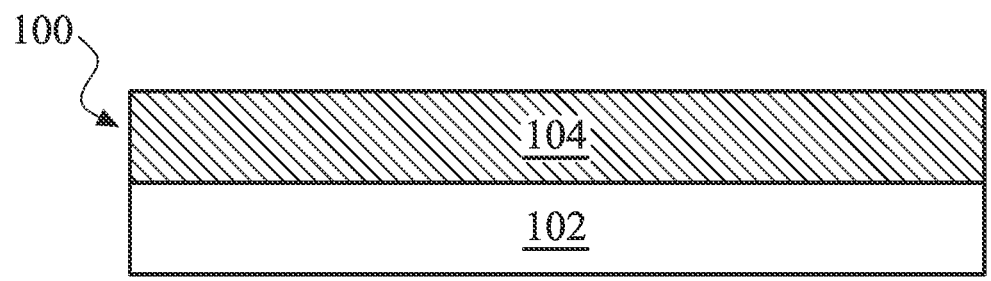
FIGS. 1A-1C illustrate a process for lithography patterning with photoresist having increased sensitivity to EUV light, according to one example of principles described herein.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

The present disclosure is generally related to methods for semiconductor device fabrication, and more particularly to compositions of photosensitive films in extreme ultraviolet (EUV) lithography and methods of using the same. In lithography patterning, after a resist film is exposed to a radiation, such as a EUV radiation (or alternatively other radiation, such as an electron beam), it is developed in a developer (a chemical solution). The developer removes portions (such as exposed portions as in a positive-tone photoresist or unexposed portions as in a negative-tone photoresist) of the resist film, thereby forming a resist pattern which may include line patterns and/or trench patterns. The resist pattern is then used as an etch mask in subsequent etching processes, transferring the pattern to an underlying material layer. Alternatively, the resist pattern is then used as an ion implantation mask in subsequent ion implantation processes applied to the underlying material layer, such as an epitaxial semiconductor layer.

Generally, to produce the smallest possible circuitry, most advanced lithography systems are designed to use light of very short wavelength such as for example, deep-ultraviolet light at a wavelength at or below 200 nm, or extreme ultraviolet (EUV) with a wavelength of about 13.5 nm. Such light sources are relatively weak, so the photosensitive films (e.g., a photoresist) need to be designed to utilize this light as efficiently as possible.

A photoresist that employs the chemical amplification is generally referred to as a "chemically amplified resist (CAR) ". A photoresist includes a polymer that resists etching or ion implantation during semiconductor fabrication. The photoresist also includes an acid generating compound (e.g., photo acid generator (PAG)), and a solvent. In some examples, the polymer also includes at least one acid labile group (ALG) that responds to acid. PAG absorbs radiation energy and generates acid. The polymer and the PAG are mixed in the solvent before the photoresist is applied to a workpiece, such as a semiconductor wafer, during a lithography process. The PAG is not sensitive to the EUV radiation. That is, advances to improve lithography efficiency (e.g., resolution/contrast, line-width-roughness, and sensitivity) encounter issues.

According to the present disclosure, the photoresist includes a sensitizer with a relatively high recombination energy and a low ionization energy. The sensitizer, when exposed to EUV light emits electrons. More specifically, the sensitizer absorbs EUV radiation and generates electrons. These electrons may then trigger the acid generation from the PAG. According to one example of principles described herein, the sensitizer has a chemical structure that has specific properties that increase the efficiency of the sensitizer. First, the sensitizer includes a low electron ionization energy. This means that it takes less energy absorbed from the EUV to generate an electron. Second, the sensitizer has a relatively high recombination energy level. This means that it is more difficult for the electron to recombine with the sensitizer. This is desirable because it is better that the electron not be recombined but instead travel to a PAG structure to trigger acid generation. Additionally, the PAG may include a structure that makes it more efficient at absorbing the electron to trigger acid generation.

In one example, the desirable characteristics of the sensitizer are achieved by having a chemical structure with a heterocyclic ring that includes at least one nitrogen atom and at least one double bond. Additionally, the desirable characteristics of the PAG may be achieved by having an absorb group with at least one ring that is heterocyclic with a carbon atom and at least one nitrogen or oxygen atom Such structures, as described in more detail below, allow for more efficient electron transfer and more efficient acid generation under EUV radiation. The photoresist and the lithography methods are further described below.

Figure 1B:
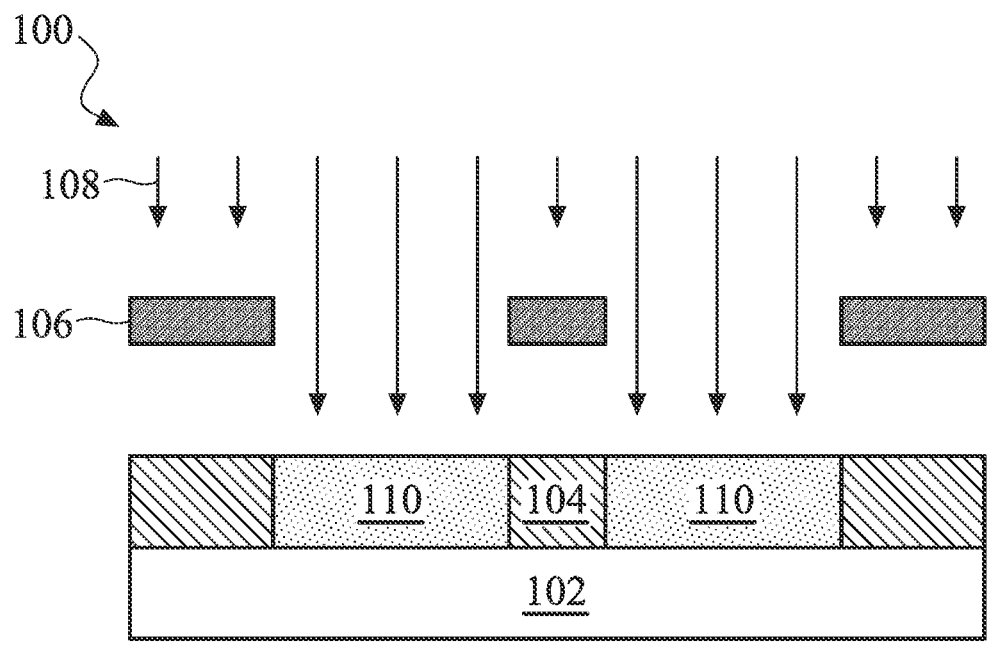
Figure 1C:
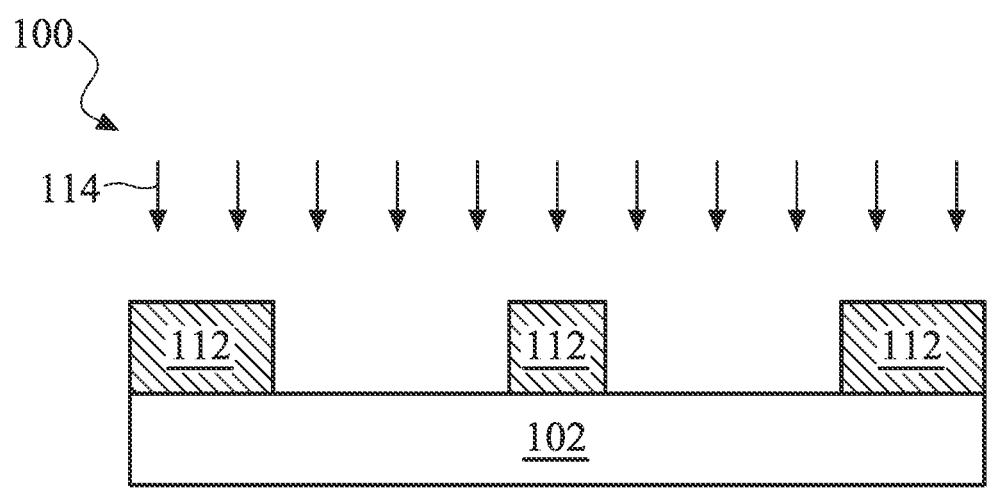

FIGS. 1A-1C illustrate a process for lithography patterning with photoresist having increased sensitivity to EUV light. As described above, the photoresist has increased sensitivity to EUV light due to the sensitizer having a higher recombination energy level and a lower ionization energy and the PAG having better absorption of electrons. FIG. 1A illustrates a photoresist layer 104 deposited onto a semiconductor structure 100. The semiconductor structure 100 may be an intermediate workpiece fabricated during processing of an IC, or a portion thereof, that may include logic circuits, memory structures, passive components (such as resistors, capacitors, and inductors), and active components such diodes, field-effect transistors (FETs), metal-oxide semiconductor field effect transistors (MOSFET), complementary metal-oxide semiconductor (CMOS) transistors, bipolar transistors, high voltage transistors, high frequency transistors, fin-like FETs (FinFETs), other three-dimensional (3D) FETs, metal-oxide semiconductor field effect transistors (MOSFET), complementary metal-oxide semiconductor (CMOS) transistors, bipolar transistors, high voltage transistors, high frequency transistors, other memory cells, and combinations thereof.

According to the present example, the semiconductor structure 100 includes a substrate 102. In one example, the substrate 102 is a semiconductor substrate (e.g., wafer). In another example, the substrate 102 includes silicon in a crystalline structure. In alternative embodiments, the substrate 102 includes other elementary semiconductors such as germanium, or a compound semiconductor such as silicon carbide, gallium arsenide, indium arsenide, and indium phosphide. The substrate 102 may include one or more layers of material or composition. The substrate 102 may include a silicon on insulator (SOI) substrate, be strained/stressed for performance enhancement, include epitaxial regions, include isolation regions, include doped regions, include one or more semiconductor devices or portions thereof, include conductive and/or non-conductive layers, and/or include other suitable features and layers.

In the present example, the substrate 102 is to be processed so as to be patterned or to be implanted. In some examples, an underlayer (not shown), such as a hard mask, may be deposited onto the substrate 102 before the resist layer 104 is deposited. In one example, the underlayer may include material(s) such as silicon oxide, silicon nitride (SiN), silicon oxynitride, or other suitable material or composition. In some examples the underlayer is an anti-reflection coating (ARC) layer such as a nitrogen-free anti-reflection coating (NFARC) layer including material(s) such as silicon oxide, silicon oxygen carbide, or plasma enhanced chemical vapor deposited silicon oxide. In some examples, the underlayer may include a high-k dielectric layer, a gate layer, a hard mask layer, an interfacial layer, a capping layer, a diffusion/barrier layer, a dielectric layer, a conductive layer, other suitable layers, and/or combinations thereof.

In some examples, the semiconductor structure 100 may be alternatively a photomask used to pattern a semiconductor wafer. In furtherance of such examples, the substrate 102 is a photomask substrate that may include a transparent material (such as quartz), or a low thermal expansion material such as silicon oxide-titanium oxide compound. The photomask substrate may further include a material layer to be patterned. To further this example, the substrate may be a photomask substrate for making a deep ultraviolet (DUV) mask, an extreme ultraviolet (EUV) mask, or other types of masks. Accordingly, the underlayer may be a material layer to be patterned to define a circuit pattern. For example, the underlayer may be an absorber layer, such as chromium layer.

The resist layer 104 is sensitive to radiation used in a lithography exposure process and has a resistance to etch (or implantation). The resist layer 104 may be formed by a spin-on coating process. In some examples, the photoresist is further treated with a soft baking process. In some examples, the resist layer 104 is sensitive to a radiation, such as I-line light, a DUV light (e.g., 248 nm radiation by krypton fluoride (KrF) excimer laser or 193 nm radiation by argon fluoride (ArF) excimer laser), a EUV light (e.g., 135 nm light), an electron beam (e-beam), and an ion beam. In the present example, the photoresist layer is sensitive to EUV radiation.

FIG. 1B illustrates an exposing process 108 to expose the resist layer 104 to a radiation beam in a lithography system. In some examples, the radiation is an EUV radiation (e.g., 13.5 nm). In some examples, the radiation may be an I-line (365 nm), a DUV radiation such as KrF excimer laser (248 nm), ArF excimer laser (193 nm), a EUV radiation, an x-ray, an e-beam, an ion beam, and/or other suitable radiations. The exposing process 108 may be performed in air, in a liquid (immersion lithography), or in a vacuum (e.g., for EUV lithography and e-beam lithography). In some examples, the radiation beam is directed to the resist layer 104 to form an image of a circuit pattern defined on a photomask, such as a transmissive mask or a reflective mask in a proper exposing mode, such as step and scan. Various resolution enhancement techniques, such as phase-shifting, off-axis illumination (OAI) and/or optical proximity correction (OPC), may be used implemented through the photomask or the exposing process. For examples, the OPC features may be incorporated into the circuit pattern. In another example, the photomask is a phase-shift mask, such as an alternative phase-shift mask, an attenuated phase-shift mask, or a chromeless phase-shift mask. In yet another example, the exposing process is implemented in an off-axis illumination mode. In some other embodiments, the radiation beam is directly modulated with a predefined pattern, such as an IC layout, without using a mask (such as using a digital pattern generator or direct-write mode). In the present embodiment, the radiation beam is a EUV radiation and the exposing process 108 is performed in an EUV lithography system, such as the EUV lithography system. Since the sensitivity of the resist layer 104 is enhanced and the exposing threshold of the resist layer may be lower than 20 mJ/cm$^2$. Accordingly, the exposing process is implemented with the dose less than 20 mJ/cm$^2$.

Due to the particular properties of the resist layer 104, the resist layer 104 more efficiently absorbs EUV light. More specifically, more electrons are generated by the sensitizer. These electrons are then more efficiently absorbed by the PAG.

After the exposing process, there may be thermal treatments in some cases. For example, a post-exposure baking (PEB) process may be applied to the semiconductor structure 100, especially to the resist layer 104 coated on the substrate 102. During the PEB process, the ALG in the exposed resist material is cleaved, the exposed portions of the resist material are changed chemically (such as more hydrophilic or more hydrophobic). In a specific embodiment, the PEB process may be performed in a thermal chamber at temperature ranging between about 120° C. to about 160° C.

After the exposing process 108, the exposed portions 110 are chemically altered such that they will either be resistant to a developer or removable by a developer. In some examples, the exposed portions 110 are de-protected, inducing polarity change for dual-tone imaging (developing). In other examples, the exposed portions 110 are changed in polymerization, such as depolymerized as in positive resist or cross-linked as in negative resist.

FIG. 1C illustrates a development process applied to the resist layer 104. By the developing process, a patterned resist layer 112 is formed. In some examples, the resist layer 104 experiences a polarity change after the exposing process 108, and a dual-tone developing process may be implemented. In some examples, if the resist layer 104 is changed from a nonpolar state (hydrophobic state) to a polar state (hydrophilic state), then the exposed portions 110 will be removed by an aqueous solvent (positive tone imaging), such as tetramethyl ammonium hydroxide (TMAH), or alternatively the unexposed portions will be removed by an organic solvent (negative tone imaging), such as butyl acetate. In some other examples, the resist layer 104 is changed from a polar state to a nonpolar state, then the exposed portions 110 will be removed by an organic solvent (positive tone imaging) or the unexposed portions will be removed by an aqueous solvent (negative tone imaging).

In the present example illustrated in FIG. 1C, the exposed portions 110 are removed in the developing process 114. In this example shown in FIG. 1C, the patterned resist layer 112 is represented by two line patterns. However, the following discussion is equally applicable to resist patterns represented by trenches.

In some examples, a fabrication process, such as an etch or implantation process, may be applied to the semiconductor structure 100 using the patterned resist layer 112 as a mask such that the fabrication process is only applied to the portions of the semiconductor structure 100 within the openings of the patterned resist layer 112 while other portions covered by the patterned resist layer 112 are protected from being impacted by the fabrication process. In some examples, the fabrication process includes an etching process applied to the material layer 102 using the patterned resist layer 112 as an etch mask, thereby transferring the pattern from the patterned resist layer 112 to the material layer 102. In some examples, the fabrication process includes an ion implantation process applied to the semiconductor structure 100 using the patterned resist layer as an implantation mask, thereby forming various doped features in the semiconductor structure 100.

In the case where a hard mask layer is positioned above the material layer 102, the pattern is first transferred from the patterned resist layer 112 to the hard mask layer, and then to the material layer 102. For example, the hard mask layer may be etched through openings of the patterned resist layer 112 using a dry (plasma) etching, a wet etching, and/or other etching methods. For example, a dry etching process may implement an oxygen-containing gas, a fluorine-containing gas, a chlorine-containing gas, a bromine-containing gas, an iodine-containing gas, other suitable gases and/or plasmas, and/or combinations thereof. The patterned resist layer 112 may be partially or completely consumed during the etching of the hard mask layer. In one example, any remaining portion of the patterned resist layer 112 may be stripped off, leaving a patterned hard mask layer over the substrate 102.

Although not shown in FIGS. 1A to 1C, the fabrication process may include other operations before, during or after the operations described above. In one example, the other operations may include forming field effect transistor (FinFET) structures. In such an example, the fabrication process may include forming a plurality of active fins in the semiconductor substrate 102. In furtherance of this example, substrate 102 may be etched through the openings of the patterned hard mask to form trenches in the substrate 102; filling the trenches with a dielectric material; performing a chemical mechanical polishing (CMP) process to form shallow trench isolation (STI) features; and epitaxy growing or recessing the STI features to form fin-like active regions. In some examples, the other operations may include forming a plurality of gate electrodes in the semiconductor substrate 102. Other operations may further include forming gate spacers, doped source/drain regions, contacts for gate/source/drain features, etc. In some examples, a target pattern is to be formed as metal lines in a multilayer interconnection structure. For example, the metal lines may be formed in an inter-layer dielectric (ILD) layer of the substrate 102, which has been etched by to form a plurality of trenches. Other operations may include filling the trenches with a conductive material, such as a metal; and further polishing the conductive material using a process such as chemical mechanical planarization (CMP) to expose the patterned ILD layer, thereby forming the metal lines in the ILD layer. The above are non-limiting examples of devices/structures that can be made and/or improved using the resist layer 104 according to various aspects of the present disclosure.

Figure 2:
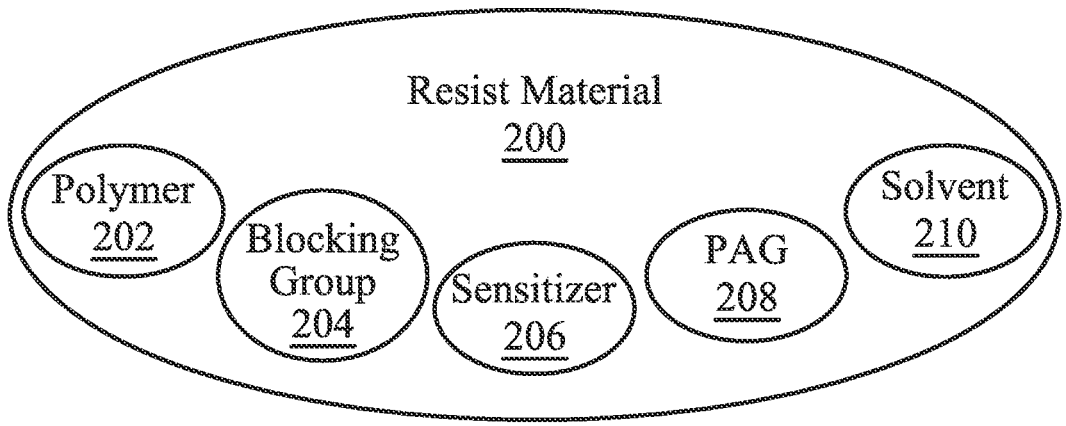
FIG. 2 is a diagram showing illustrative components of a photoresist that has increased sensitivity to EUV light, according to one example of principles described herein.

FIG. 2 is a diagram showing illustrative components of a photoresist that has increased sensitivity to EUV light. In the present example, the photoresist 300 utilizes a chemical amplification (CA) photoresist material. In one example, the CA resist material is positive tone and includes a polymer material that turns soluble to a developer after the polymeric material is reacted with acid. In another example, the CA resist material is negative tone and includes a polymer material that turns insoluble to a developer such as a base solution after the polymer is reacted with acid. In yet another example, the CA resist material includes a polymer material that changes its polarity after the polymer is reacted with acid.

The resist material 200 is sensitive extreme ultraviolet (EUV) light. The resist material 200 includes a polymer 202, a blocking group 204 chemically bonded to the polymer 202, a sensitizer 206, and an Acid Generating Compound (AGC) such as a Photo-Acid Generator (PAG) 208. The resist material 200 further includes solvent 210 with the above chemicals mixed therein. The sensitizer 206 may be blended with or bonded to the polymer 202, or bonded to the AGC 208. In some embodiments, the resist material 200 may include other additives, such as quencher.

Figures 4, 5:
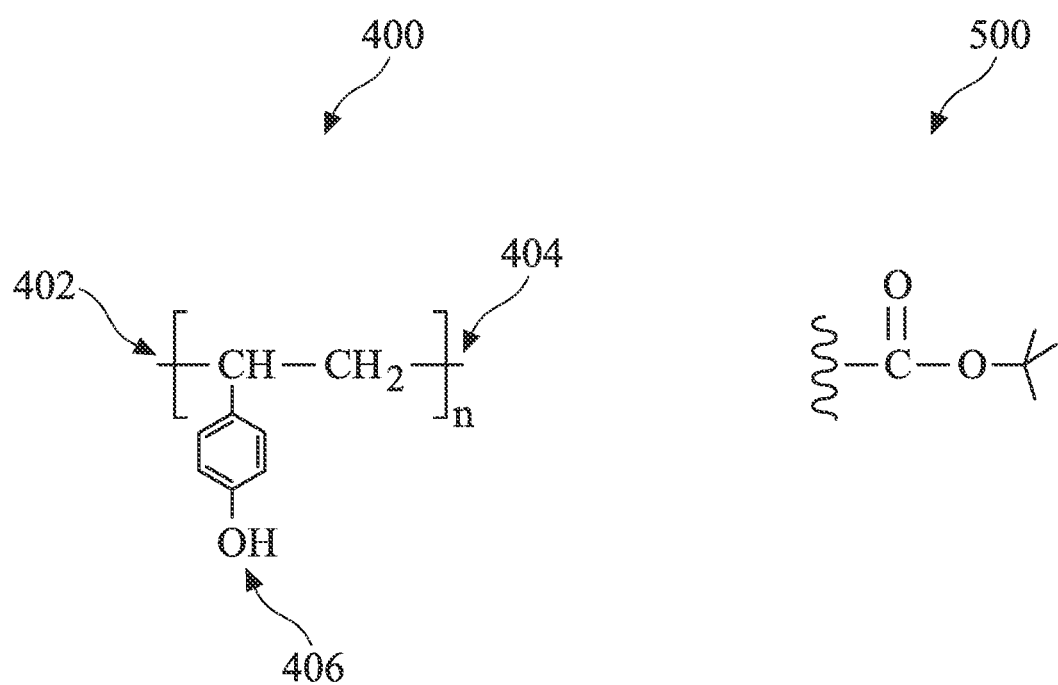
FIG. 4 is a diagram showing an illustrative polymer structure that may be used in a photoresist with increased sensitivity to EUV light, according to one example of principles described herein.
FIG. 5 is a diagram showing an illustrative blocking structure that may be used in a photoresist with increased sensitivity to EUV light, according to one example of principles described herein.

The polymer 202 provides resistance to etch (or implantation). In various examples, the polymer 202 includes a poly(norbornene)-co-malaic anhydride (COMA) polymer, a polyhydroxystyrene (PHS) polymer, or an acrylate-based polymer. For example, the acrylate-based polymer includes a poly (methyl methacrylate) (PMMA) polymer. The PHS polymer includes a plurality of PHS chemical structure 400 shown in FIG. 4, in which n is an integer greater than 2. The PHS chemical structure 400 includes two ends 402 and 404 that are chemically linkable ends of other PHS chemical structures. Furthermore, PHS is also sensitive to EUV and is able to function as sensitizer for EUV resist. Accordingly, a plurality of the chemical structures 400 are chemically bonded together (through the two ends 402 and 404), thereby forming a PHS polymeric backbone. The polymer 202 also includes multiple side locations that may chemically bond with other chemical groups. For example, the PHS polymer includes a plurality of hydroxyl (OH) groups 406 chemically bonded to side locations.

In some examples, the resist material 200 further includes a blocking group 204, such as acid labile group (ALG) or dissolution inhibitor that responds to acid. The blocking group 204 is a chemical group that is deprotected by PAG in exposed areas of the resist layer. Thus, the exposed resist material 200 will change the polarity and dissolubility. For example, the exposed resist material has an increased dissolubility in a developer (for a positive-tone resist) or decreased dissolubility in a developer (for a negative-tone resist). When the exposing dose of the lithography exposing process reaches a dose threshold, the exposed resist material will be dissoluble in the developer or alternatively the exposed resist material will be insoluble in the developer. In one example, the blocking group 204 includes a t-butoxy-cardbonyl (tBOC) 500 illustrated in FIG. 5.

The resist material 200 further includes a sensitizer 206 to increase the sensitivity and efficiency of the resist material. The sensitizer 206 is designed to increase the sensitivity of the resist material. A resist material may not be sensitive to EUV but is more sensitive to electrons or other radiation, such UV or DUV. Thus, by incorporating the sensitizer 206, the resist material has an enhanced sensitivity to the first radiation. Particularly, the sensitizer 206 is sensitive to the first radiation and be able to generate a second radiation in response to the first radiation. In the present embodiment, the first radiation is EUV radiation and the second radiation is electron(s). The sensitizer 206 absorbs EUV radiation and generates secondary electron. Furthermore, the acid generating compound 208 is sensitive to the secondary electron, absorbs the secondary electron and generates acid.

In some embodiments, the sensitizer 206 is mixed with the polymer 202 and PAG 208 in the solvent 210. In some embodiments, the sensitizer 206 is alternatively or additionally bonded to the polymer 202 or the PAG 208. In various examples, the sensitizer 206 may be monomer additive, oligomer and polymer type in photoresist.

Figure 3A:
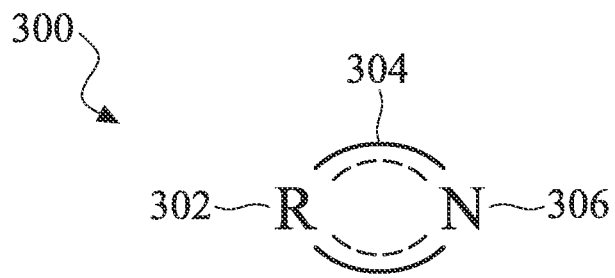
FIGS. 3A and 3B illustrate various characteristics of a sensitizer for a photoresist with increased sensitivity to EUV light, according to one example of principles described herein.
Figure 3B:
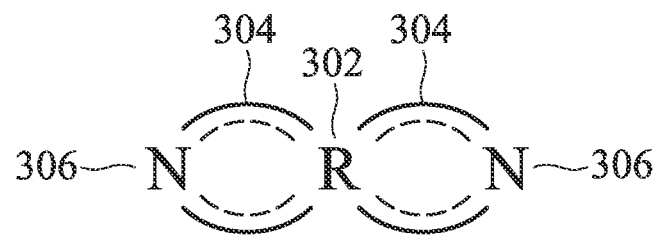

According to one example of principles described herein, the sensitizer includes a heterocyclic ring that includes at least one nitrogen atom and at least one double bond. In some examples, the sensitizer has a recombination energy within a range of about 165-170 kilocalories/mol. FIGS. 3A and 3B illustrate various double bonds 304 between a nitrogen atom 306 and R 302, which may be a C4~C30 resonance ring, aromatic, or heterocyclic aromatic. R 302 may also can contain a polar group such as —OH, —NH2, —COOH, —CONH2. Such a structure provides the sensitizer 206 with a lower ionization energy and higher recombination energy. FIG. 3A illustrates an example in which there is one nitrogen atom bonded to a resonance ring. FIG. 3B illustrates an example in which there are two nitrogen atoms bonded to a resonance ring.

The resist material 200 includes an acid generating compound (AGC) 208, such as photoacid generator (PAG), so also referred to as PAG 208. The acid generating compound 208 absorbs radiation energy and generates acid. The resist material 200 also includes a solvent 210. The polymer 202 and the acid generating compound 208 are mixed in the solvent 210 before the resist material is applied to a workpiece, such as a semiconductor wafer, during a lithography process.

The PAG 208 includes a phenyl ring. In a particular example, the PAG 208 includes a sulfonium cation, such as a triphenylsulfonium (TPS) group; and an anion, such as a triflate anion. Particularly, the cation of the PAG has a chemical bond to a sulfur and an additional chemical bond such that the sensitivity (or absorption) of the PAG to the electron, or other type of the second radiation, is increased.

In some embodiments, the PAG 208 is designed with chemical structure to effectively absorb EUV radiation. For examples, the PAG 208 may include fluorine, saturated alkyl group, aromatics, heterocyclic group or a combination to enhance the EUV absorption. In some examples, the sensitizer 206 is chemically bonded to PAG 208.

In some examples, the PAG 208 is designed to have specific chemical structures to better absorb electrons generated by the sensitizer 206. Specifically, the PAG may include at least one heterocyclic ring having at least one nitrogen or oxygen atom in addition to several carbon atoms. The PAG 208 may also have at least one double bond within that heterocyclic ring. Various examples of such PAG structures are shown in FIGS. 7A-7D as well as FIGS. 8A-8H.

FIGS. 7A-7D illustrate PAG structures that have a structure M+ that is surrounded by a number of heterocyclic structures. Such heterocyclic structures are indicated by R1, R2, R3, R4, R5, R6, and R7. R1, R2, R3, R4, R5, R6, and R7 may include at least one of C1~C20 heterocyclic aromatics derivatives (e.g., Furan, Pyridine, Pyrazine, Imidazole, thiophene) and fluoro alkyl groups. In some examples, M may be a cation and A may be an anion. In some examples, M or A may be one of Sulfur (S), Carbon (C), or Iodine (I).

FIGS. 8A-8H illustrate various PAG structures that have a structure surrounded by a number of rings. In the present example, the structure is a sulfur cation. As illustrated, each structure has at least one heterocyclic ring with at least one double bond. In some examples, there are at least two double bonds. In some examples, there are three double bonds.

Figure 6A:
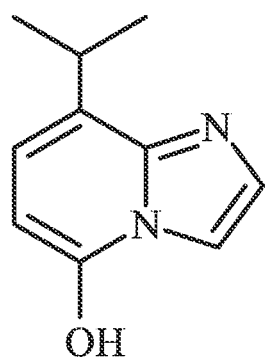
FIGS. 6A and 6B show illustrative chemical structures of a sensitizer for a photoresist with increased sensitivity to EUV light, according to one example of principles described herein.
Figure 6B:
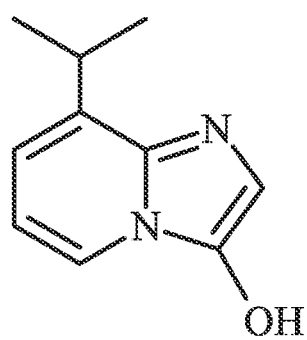
Figure 7A:
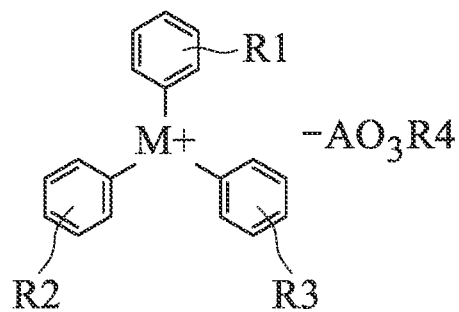
FIGS. 7A, 7B, 7C, and 7D show illustrative chemical structures of a PAG for a photoresist with increases sensitivity to EUV light, according to one example of principles described herein.
Figure 7B:
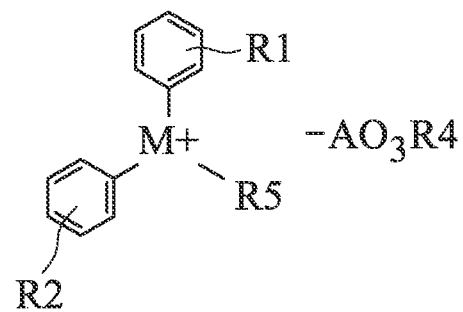
Figure 7C:
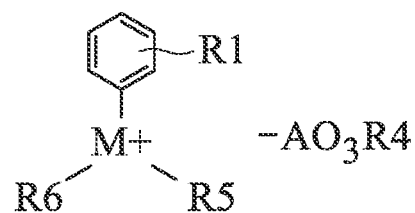
Figure 7D:
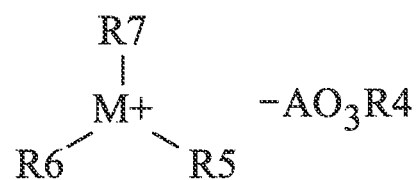
Figure 8A:
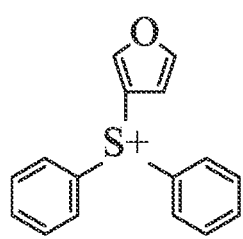
FIGS. 8A, 8B, 8C, 8D, 8E, 8F, 8G, and 8H show additional illustrative chemical structures of a PAG for a photoresist with increases sensitivity to EUV light, according to one example of principles described herein.
Figure 8B:
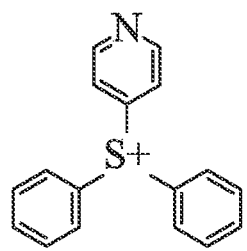
Figure 8C:
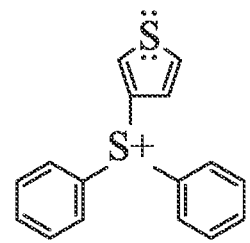
Figure 8D:
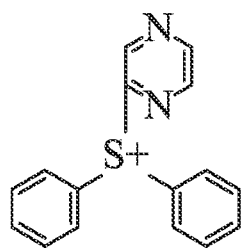
Figure 8E:
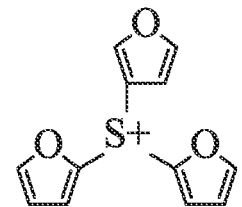
Figure 8F:
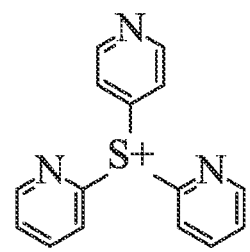
Figure 8G:
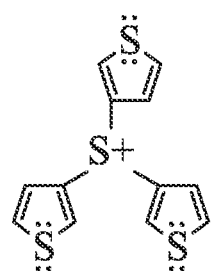
Figure 8H:
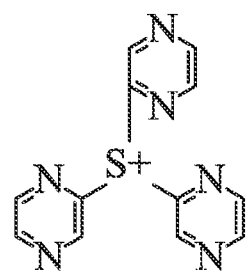
Figure 9:
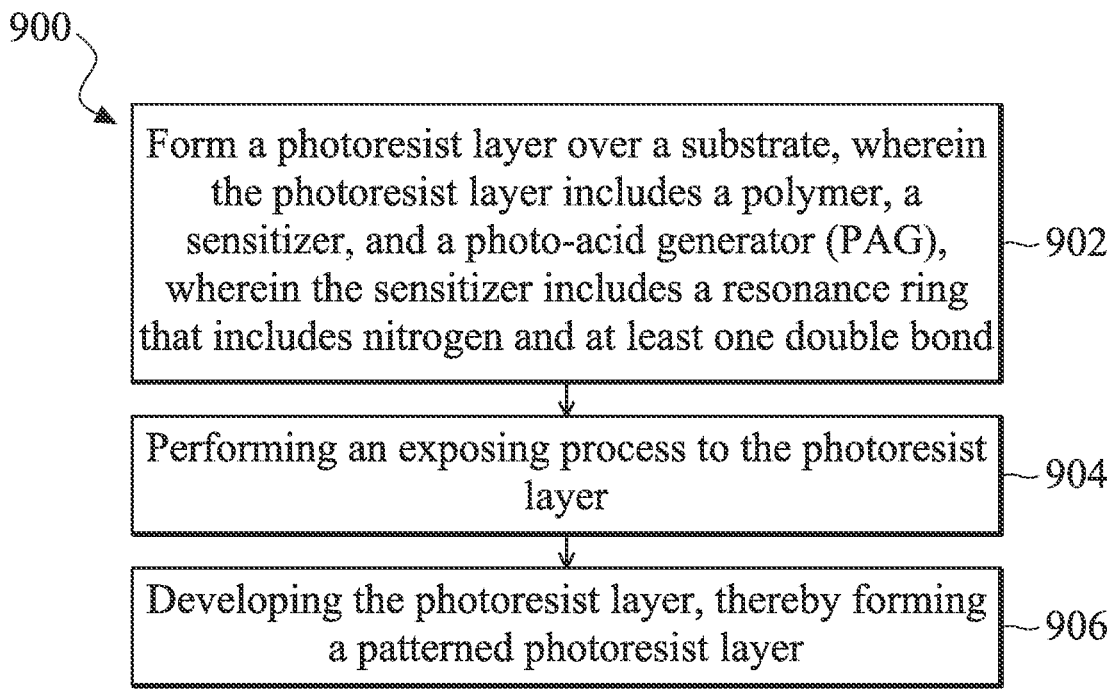
FIG. 9 is a flowchart showing an illustrative method of using a photoresist having a sensitizer that improves the photoresist's sensitivity to EUV light, according to one example of principles described herein.

FIG. 9 is a flowchart showing an illustrative method of using a photoresist having a sensitizer that improves the photoresist's sensitivity to EUV light. According to one example, the method includes a process 902 for forming a photoresist layer over a substrate, wherein the photoresist layer includes a polymer, a sensitizer, and a photo-acid generator (PAG), wherein the sensitizer includes a resonance ring that includes nitrogen and at least one double bond. For example, the sensitizer may have a structure like the ones illustrated in FIGS. 6A and 6B. The method further includes a process 904 for performing an exposing process to the photoresist layer. Such an exposing process may be as described above in the text accompanying FIG. 1B. The method further includes a process 906 for developing the photoresist layer, thereby forming a patterned photoresist layer. The developing process may be as described above in the text accompanying FIG. 1C.

Figure 10:
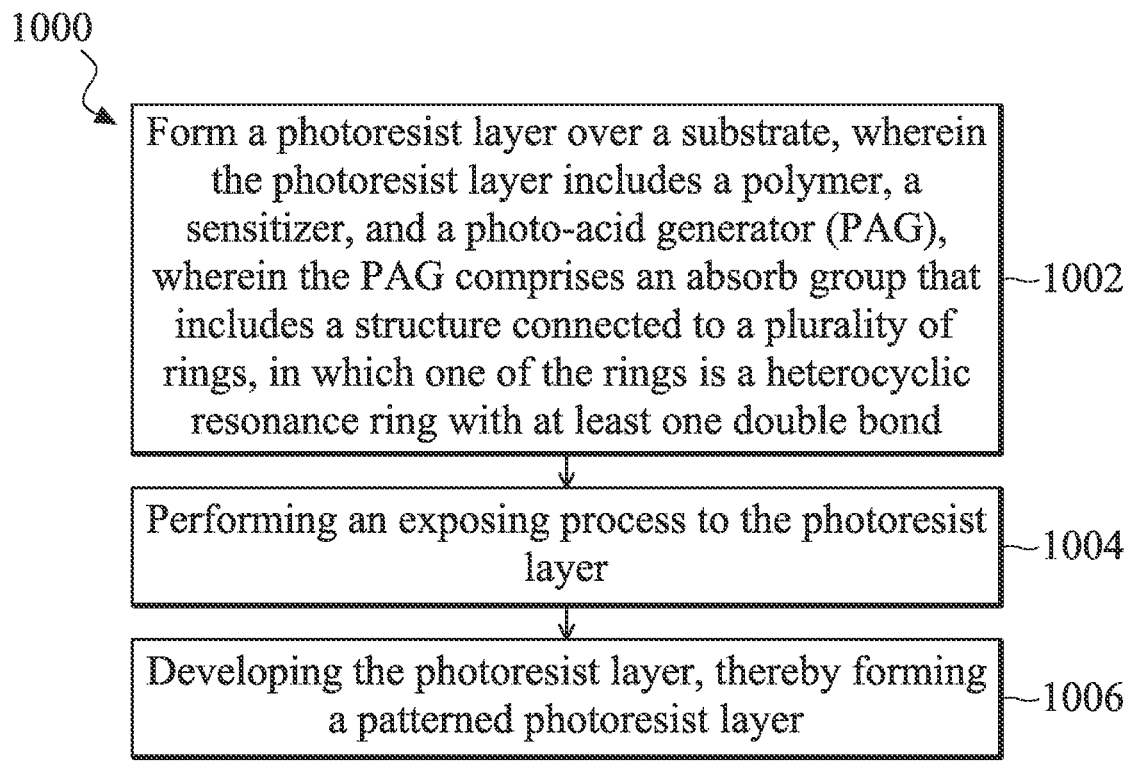
FIG. 10 is a flowchart showing an illustrative method of using a photoresist having a PAG that improves the photoresist's sensitivity to EUV light, according to one example of principles described herein.

FIG. 10 is a flowchart showing an illustrative method of using a photoresist having a PAG that improves the photoresist's sensitivity to EUV light. According to one example, the method 1000 includes a process 1002 for forming a photoresist layer over a substrate, wherein the photoresist layer includes a polymer, a sensitizer, and a photo-acid generator (PAG), wherein the sensitizer includes a resonance ring that includes nitrogen and at least one double bond. The PAG may have a structure like the structures illustrated in FIGS. 7A-7D and FIGS. 8A-8H. The method further includes a process 1004 for performing an exposing process to the photoresist layer. Such an exposing process may be as described above in the text accompanying FIG. 1B. The method further includes a process 1006 for developing the photoresist layer, thereby forming a patterned photoresist layer. The developing process may be as described above in the text accompanying FIG. 1C.

The present disclosure provides a photoresist material with enhanced sensitivity and a lithography method using the same. The resist material includes a polymer, a sensitizer and a PAG mixed in a solvent. More specifically, the PAG includes a chemical structure for increased EUV absorption or the sensitizer has a chemical structure for increased EUV absorption. Accordingly, the sensitivity of the resist material is enhanced.

According to one example, a method includes forming a photoresist layer over a substrate, wherein the photoresist layer includes a polymer, a sensitizer, and a photo-acid generator (PAG), wherein the sensitizer includes a resonance ring that includes nitrogen and at least one double bond. The method further includes performing an exposing process to the photoresist layer. The method further includes developing the photoresist layer, thereby forming a patterned photoresist layer.

According to one example, a method includes forming a photoresist layer over a substrate, wherein the photoresist layer includes a polymer, a sensitizer, and a photo-acid generator (PAG), wherein the PAG comprises an absorb group that includes a structure with a plurality of rings, in which one of the rings is a heterocyclic resonance ring with at least one double bond. The method further includes performing an exposing process to the photoresist layer. The method further includes developing the photoresist layer, thereby forming a patterned photoresist layer.

According to one example, a method includes forming a photoresist layer over a substrate. The photoresist layer includes a polymer, a sensitizer that includes a resonance ring that includes nitrogen and at least one double bond, and a photo-acid generator (PAG), wherein the PAG comprises an absorb group that includes a structure with a plurality of rings, in which one of the rings is a heterocyclic resonance ring with at least one double bond. The method further includes performing an exposing process to the photoresist layer and developing the photoresist layer, thereby forming a patterned photoresist layer.

The foregoing outlines features of several embodiments so that those of ordinary skill in the art may better understand the aspects of the present disclosure. Those of ordinary skill in the art should appreciate that they may readily use the present disclosure as a basis for designing or modifying other processes and structures for carrying out the same purposes and/or achieving the same advantages of the embodiments introduced herein. Those of ordinary skill in the art should also realize that such equivalent constructions do not depart from the spirit and scope of the present disclosure, and that they may make various changes, substitutions, and alterations herein without departing from the spirit and scope of the present disclosure.

What is claimed is:
1. A method, comprising:
    forming a photoresist layer over a substrate, wherein the photoresist layer includes a polymer responsive to an acid, a photo-acid generator (PAG), and a sensitizer bonded to the polymer, wherein the sensitizer includes an imidazole ring and a hydroxy, wherein the hydroxy is attached to a carbon atom in the imidazole ring, wherein the carbon atom is directly bonded to a nitrogen atom in the imidazole ring, wherein the PAG includes a sulfonium cation or an iodonium cation, wherein the PAG further includes a heterocyclic ring directly bonded to the sulfonium cation or the iodonium cation, and wherein the heterocyclic ring includes one nitrogen atom and less than six carbon atoms;

performing an exposing process to the photoresist layer; and developing the photoresist layer, thereby forming a patterned photoresist layer.

2. The method of claim 1, wherein the heterocyclic ring is a first heterocyclic ring, wherein the PAG further includes a second heterocyclic ring different from the first heterocyclic ring directly bonded to the sulfonium cation or the iodonium cation.

3. The method of claim 2, wherein the PAG further includes a third heterocyclic ring directly bonded to the sulfonium cation, wherein the third heterocyclic ring is different from the first heterocyclic ring and the second heterocyclic ring.

4. The method of claim 3, wherein the first heterocyclic ring includes four carbon atoms and an oxygen atom.

5. The method of claim 3, wherein the second heterocyclic ring includes five carbon atoms and a nitrogen atom.

6. The method of claim 3, wherein the third heterocyclic ring has four carbon atoms and two nitrogen atoms.

7. The method of claim 6, wherein the two nitrogen atoms are bonded by two of the four carbon atoms there between.

8. The method of claim 1, wherein the heterocyclic ring is a first heterocyclic ring, wherein the PAG further includes a second heterocyclic ring and a third heterocyclic ring both directly bonded to the sulfonium cation, wherein the first heterocyclic ring, the second heterocyclic ring, and the third heterocyclic ring have the same structure.

9. The method of claim 1, wherein the PAG includes a structure selected from structures (A)-(H) below:

(A)
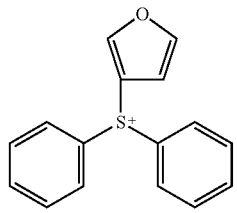

(B)
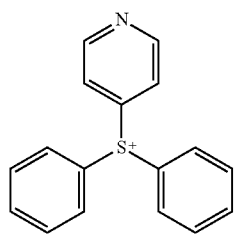

(C)
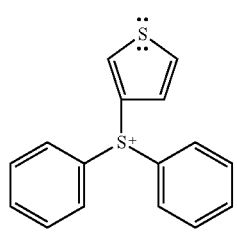

(D)
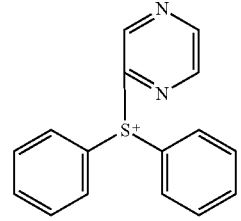

(E)
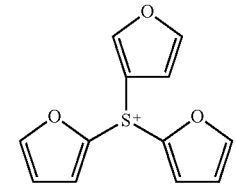

(F)
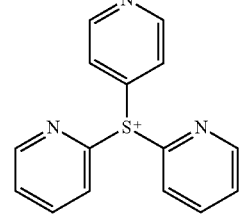

(G)
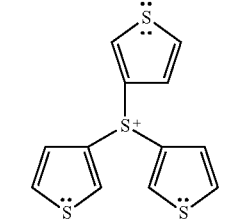

(H)
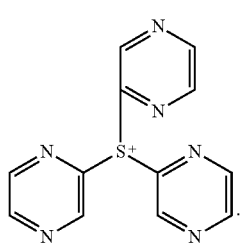

10. The method of claim 9, wherein the sensitizer includes a structure below:

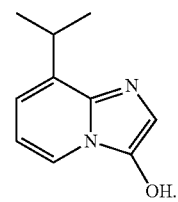

11. A method, comprising:

forming a photoresist layer over a substrate, wherein the photoresist layer includes a polymer having an acid labile group, a photo-acid generator (PAG), a sensitizer bonded to the polymer, wherein the PAG includes a sulfonium cation and three heterocyclic rings directly bonded to the sulfonium cation, and wherein the sensitizer includes an imidazole ring fused with a pyridine ring and a hydroxyl group bonded to a carbon atom adjacent to a nitrogen atom in the imidazole ring;

performing an exposing process to the photoresist layer; and developing the photoresist layer, thereby forming a patterned photoresist layer.

12. The method of claim 11, wherein the sensitizer further includes a propyl group bonded to a first carbon atom, and wherein the first carbon atom and two nitrogen atoms are bonded to a second carbon atom.

13. The method of claim 12, wherein the hydroxyl group and the propyl group are bonded to the pyridine ring.

14. The method of claim 13, wherein the hydroxyl group and the propyl group are bonded together by four carbon atoms.

15. The method of claim 11, wherein the sensitizer includes structured (A) and (B) below:

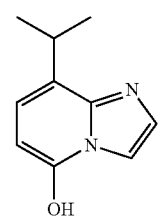
(A)

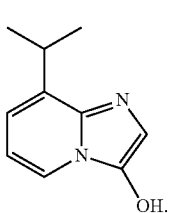
(B)

16. The method of claim 15, wherein the PAG bonded to the sensitizer includes structured (C)-(J) below:

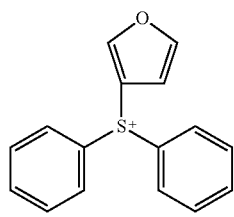
(C)

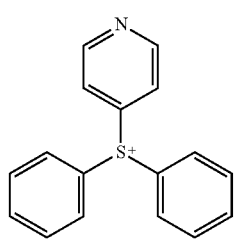
(D)

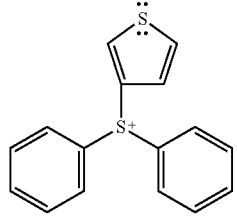
(E)

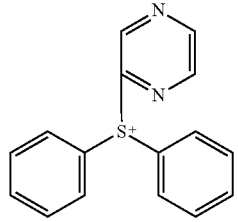
(F)

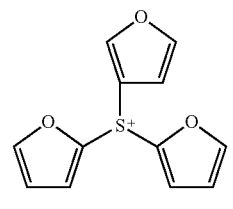
(G)

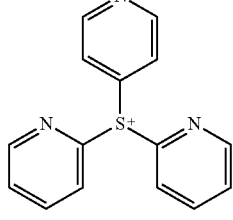
(H)

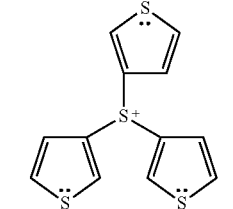
(I)

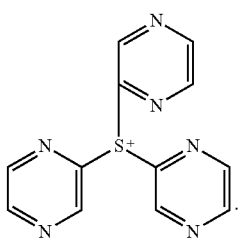
(J)

17. A method, comprising:
forming a photoresist layer over a substrate, wherein the photoresist layer includes a polymer responsive to an acid, a photo-acid generator (PAG), and a sensitizer bonded to the polymer, wherein the sensitizer includes an imidazole ring and a hydroxy bonded to a carbon atom adjacent to a nitrogen atom in the imidazole ring, wherein the PAG includes a sulfonium cation and three heterocyclic rings directly bonded to the sulfonium cation;

performing an exposing process to the photoresist layer; and developing the photoresist layer, thereby forming a patterned photoresist layer.

18. The method of claim 17, wherein the imidazole ring is fused with a pyridine; and each of the heterocyclic rings includes one nitrogen atom and less than six carbon atoms.

19. The method of claim 17, wherein the PAG includes a structure selected from structures (A)-(H) below:

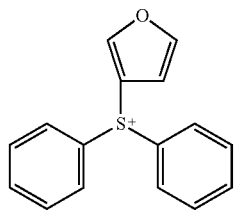
(A)

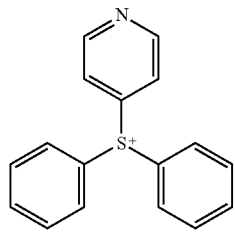
(B)

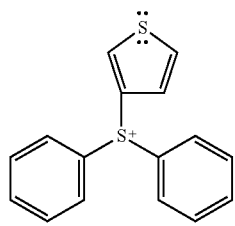
(C)

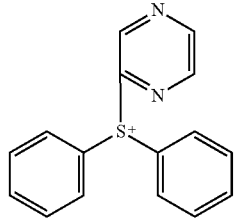
(D)

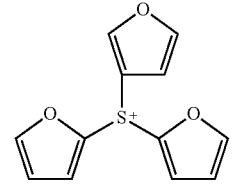
(E)

-continued

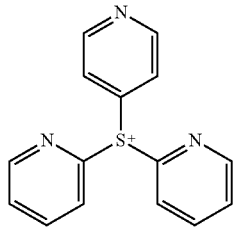
(F)

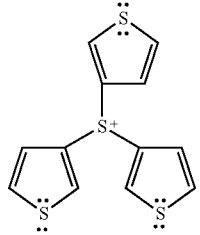
(G)

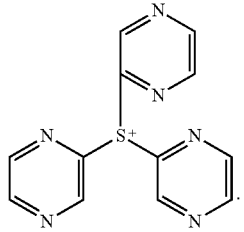
(H)

20. The method of claim 17, wherein the sensitizer includes a structure selected from structured (I)-(J) below:

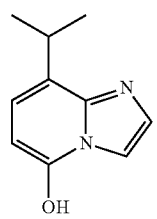
(I)

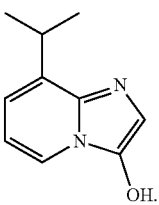
(J)

* * * * *